United States Patent [19]
Kirby et al.

[11] Patent Number: 5,569,742
[45] Date of Patent: Oct. 29, 1996

[54] CENTRALLY TRUNCATED NPY CYCLIC PEPTIDES

[75] Inventors: Dean A. Kirby, San Diego; Jean E. F. Rivier, La Jolla, both of Calif.

[73] Assignee: The Salk Institute for Biological Studies, San Diego, Calif.

[21] Appl. No.: 264,030

[22] Filed: Jun. 22, 1994

[51] Int. Cl.$^6$ .............................. C07K 7/64; A61K 38/12
[52] U.S. Cl. .................. 530/317; 530/323; 530/321; 530/318
[58] Field of Search .................. 514/11, 9, 2; 530/317, 530/323, 321, 318

[56] References Cited

U.S. PATENT DOCUMENTS 5,026,685  6/1991  Boublik et al. .............................. 514/13
5,328,899  7/1994  Boublik et al. .............................. 514/13

OTHER PUBLICATIONS

Sheikh et al., "Y$_1$ and Y$_2$ receptors for neuropeptide Y", *Elsevier Science Publishers B.V., FEBS Letters*, vol. 245, No. 1,2, pp. 209–214, Mar. 1989.

Boublik et al., "Synthesis and Hypertensive Activity of Neuropeptide Y Fragments and Analogues with Modified N– or C–Termini or D–Substitutions", *Jorunal of Medicinal Chemistry*, vol. 32, No. 3, pp. 597–601 (1989).

Fuhlendorff et al., "[Leu$^{31}$, Pro$^{34}$]Neuropeptide Y: A specific Y$_1$ receptor agonist", *Proc. Natl. Acad. Sci. USA 87*, pp. 182–186 (1990).

Fuhlendorff et al., "The Antiparallel Pancreatic Polypeptide Fold in the Binding of Neuropeptide Y to Y$_1$ and Y$_2$ Receptors", *Journal of Biological Chemistry*, pp. 11706–11712 (1990).

Michel, "Receptors for neuropeptide Y: multiple subtypes and multiple second messengers", *Elsevier Science Publishers Ltd (UK)*, pp. 389–394 (1991).

Beck–Sickinger et al., "A novel cyclic analog of neuropeptide Y specific for the Y$_2$ receptor", *Eur. J. Biochem.*, 206, FEBS 1992, pp. 957–964.

Kirby et al., "Structure–activity relationships of conformationally restricted deletion analogs of neuropeptide Y", *Peptides Chemistry and Biology*, pp. 480–481 (1992).

Kirby et al. Abstract P409, "High Affinity, Truncated, Cyclic and Branched Analogs of Neuropeptide Y", *Thirteenth American Peptide Symposium*, Edmondton Convention Centre, Jun. 20–25, 1993.

Bouvier et al., J. Med. Chem., vol. 35, pp. 1145–1155, (1992).

Cox et al., Peptides, vol. 12, pp. 323–327, (1991).

Reymond et al., J. Med. Chem., vol. 35, pp. 3653–3659, (1992).

*Primary Examiner*—Christina Y. Chan
*Assistant Examiner*—T. D. Wessendorf
*Attorney, Agent, or Firm*—Fitch, Even, Tabin & Flannery

[57] ABSTRACT

Centrally truncated NPY cyclic peptide analogs are described which have selective bioactivity for NPY Y1 receptors. Methods are provided for diagnosing physiological disorders manifested by abnormal levels of endogenous Y1 receptors, by means of measuring the amount of a NPY Y1 specific cyclic peptide analog which binds to a biological sample, and by means of administering a radiolabelled NPY Y1 specific cyclic peptide analog to a host subject followed by radiographic imaging. A method is further provided for therapeutic use of the cyclic peptide NPY analogs in clinical treatment of hypotension and anorexia.

5 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 36 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Tyr Pro Ser Lys Pro Asp Asn Pro Gly Glu Asp Ala Pro Ala Glu Asp
   1               5                   10                  15

Leu Ala Arg Tyr Tyr Ser Ala Leu Arg His Tyr Ile Asn Leu Ile Thr
                   20                  25                  30

Arg Gln Arg Tyr
                35

( 2 ) INFORMATION FOR SEQ ID NO:2:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:2:

Tyr Pro Ser Lys Pro Asp Xaa Xaa Xaa Xaa Xaa Xaa Xaa Ser Ala Leu
   1               5                   10                  15

Arg His Tyr Ile Asn Leu Ile Thr Arg Pro Arg Tyr
                   20                  25

( 2 ) INFORMATION FOR SEQ ID NO:3:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:3:

Tyr Pro Ser Lys Pro Asp Xaa Pro Gly Ala Arg Tyr Xaa Ser Ala Leu
   1               5                   10                  15

Arg His Tyr Ile Asn Leu Ile Thr Arg Pro Arg Tyr
                   20                  25

( 2 ) INFORMATION FOR SEQ ID NO:4:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: unknown (i i) MOLECULE TYPE: peptide (x i) SEQUENCE DESCRIPTION: SEQ ID NO:4:

```
Tyr Pro Ser Lys Pro Asp Cys Xaa Xaa Ala Arg Tyr Cys Ser Ala Leu
1               5                   10                  15

Arg His Tyr Ile Asn Leu Ile Thr Arg Pro Arg Tyr
            20                  25
```

(2) INFORMATION FOR SEQ ID NO:5:

(i) SEQUENCE CHARACTERISTICS:
        (A) LENGTH: 28 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:5:

```
Tyr Pro Ser Lys Pro Asp Cys Pro Gly Ala Arg Tyr Cys Ser Ala Leu
1               5                   10                  15

Arg His Tyr Ile Asn Leu Ile Thr Arg Pro Arg Tyr
            20                  25
```

(2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:6:

```
Tyr Pro Ser Lys Pro Asp Xaa Xaa Xaa Xaa Ser Ala Leu Arg His Tyr
1               5                   10                  15

Ile Asn Leu Ile Thr Arg Pro Arg Tyr
            20                  25
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:7:

```
Tyr Pro Ser Lys Pro Asp Xaa Pro Gly Xaa Ser Ala Leu Arg His Tyr
1               5                   10                  15

Ile Asn Leu Ile Thr Arg Pro Arg Tyr
            20                  25
```

(2) INFORMATION FOR SEQ ID NO:8:

(i) SEQUENCE CHARACTERISTICS:
        (A) LENGTH: 25 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:8:

-continued

```
Tyr Pro Ser Lys Pro Asp Cys Pro Gly Cys Ser Ala Leu Arg His Tyr
1               5                   10                  15

Ile Asn Leu Ile Thr Arg Pro Arg Tyr
            20              25
```

(2) INFORMATION FOR SEQ ID NO:9:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TACCCCTCCA AGCCGGACTG CCCGGGCGCC AGATACTGCT CGGCGCTGCG ACACTACATC      60

AACCTCATCA CCAGGCCCAG ATAT                                            84
```

(2) INFORMATION FOR SEQ ID NO:10:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:10:

```
Tyr Pro Ser Lys Pro Asp Asp Pro Gly Ala Arg Tyr Xaa Ser Ala Leu
1               5                   10                  15

Arg His Tyr Ile Asn Leu Ile Thr Arg Pro Arg Tyr
            20                  25
```

(2) INFORMATION FOR SEQ ID NO:11:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:11:

```
Tyr Pro Ser Lys Pro Asp Asp Pro Gly Xaa Ser Ala Leu Arg His Tyr
1               5                   10                  15

Ile Asn Leu Ile Thr Arg Pro Arg Tyr
            20              25
```

CENTRALLY TRUNCATED NPY CYCLIC PEPTIDES

This invention was made with Government support under Grant HL-41910 awarded by the National Institutes of Health. The Government has certain rights in this invention.

This invention is generally directed to the field of Neuropeptide Y (NPY) and to methods of diagnosis and pharmaceutical treatment using NPY analogs. More specifically, the invention relates to a family of NPY cyclic peptide analogs which are biologically selective for the NPY Y1 receptor, to methods of diagnosing physiological disorders, and to methods for treatment of hypotension and anorexia.

BACKGROUND OF THE INVENTION

Neuropeptide Y (NPY) is a 36 residue C-terminally amidated polypeptide neurotransmitter which is evolutionarily well conserved among mammals. NPY is also the most abundant peptide in the mammalian brain and is found in many central and peripheral neurons, largely co-localized with catecholamines. NPY is anatomically co-distributed and co-released with norepinephrine in and from sympathetic postganglionic neurons. NPY possesses potent vasoconstrictor properties, stimulates food intake and body fat stores, reduces heart rate, increases blood pressure, mediates analgesia, regulates memory processing, and is implicated in the pathology of various disease states, including hypertension, congestive heart failure, obesity and various psychiatric disorders. NPY can act pre-synaptically to inhibit its own release and that of catecholamines, or can potentiate the vasoconstrictor action of other neurotransmitters and hormones such as noradrenaline, angiotensin II and histamine.

NPY exerts its physiological effects by acting on specific biological receptors. Specific NPY binding sites exist in two distinct receptor subtypes, i.e., NPY receptor Y1 and NPY receptor Y2. Postsynaptic NPY receptors are of Y1 and Y2 types, whereas presynaptic receptors are mainly of the Y2 type. Subtype Y1 receptors exist in the sympathetic nervous system predominantly post-synaptically to mediate vasoconstriction and appetite stimulation. Y2 receptors, which are predominant in the central nervous system, act pre-synaptically in the regulation of catecholamine release. An extremely important action of NPY Y2 activation is to decrease cardiac contractility (inotropy). Under many circumstances in which inotropy is decreased, diseases of life-threatening importance, e.g. congestive heart failure and cardiogenic shock, are associated with increased release of NPY into the blood. Use of a selective NPY Y1 agonist to treat hypotension and various forms of shock while avoiding further NPY release is considered to be clinically beneficial in cardiac disorders.

Functional Y1 receptors have been identified on the neuroblastoma cell line SK-N-MC (Gordon, E. A. et al., J. Neurochem., 55:506–513). Functional Y2 receptors have been identified on the cell line SK-N-BE2. At the intracellular level NPY stimulation of Y2 receptors inhibits the activity of adenylate cyclase. Vascular smooth muscle contraction and centrally evoked food intake (appetite stimulation) are predominantly mediated by NPY Y1 receptors.

Distinct structure-activity relationships exist for NPY binding to different biological receptors. The distinction between the two types of receptors is derived from differential binding properties of NPY C-terminal fragments and various modifications of the peptide. Sheikh, S. P., et al. first characterized the Y1 and Y2 NPY-binding sites (FEBS 245:209–214 (1989)). It was reported that, unlike intact NPY, the NPY[13-36] C-terminal fragment binds Y2 but not Y1. Synthesis of NPY analogs with modified N- or C-termini or D-substitutions was further performed to determine the domains responsible for biological activities of the separate receptors (Boublic, J. H., et al., J. Med. Chem., 32:597–601 (1989)). An otherwise intact NPY peptide having substituted amino acids Leu$^{31}$ and Pro$^{34}$ was shown to be Y1 selective (Fuhlendorff, J., et al., PNAS 87:182–186 (1990)). Several cyclic and centrally truncated analogs of NPY have been reported that show selectivity for Y2 receptors (Beck-Sickinger, A. G., et al., Eur. J. Biochem., 206:957–964 (1992); Kirby, D. A., et al., J. Med. Chem., 36:385–393 (1993)). Improvement of Y1 binding affinity has previously been achieved only by including more residues in the central polypeptide fold (PP-fold) region, while the length of an intramolecular bridge has not previously been shown to affect binding.

Accordingly, there remains a need for stable and potent NPY analogs capable of binding and activating NPY Y1 receptors without substantially binding and activating NPY Y2 receptors in order to mediate appetite stimulation, vasoconstriction, and to detect and localize neuroblastoma tumors without affecting catecholamine release or otherwise propagating physiological effects associated with the activation of Y2 receptors.

SUMMARY OF THE INVENTION

Centrally truncated NPY cyclic peptides analogs having selective activity for NPY Y1 receptors are defined by the formulae: Tyr-Pro-Ser-Lys-Pro-Asp-Xaa$_7$-Xaa$_8$-Xaa$_9$-Xaa$_{10}$-Xaa$_{11}$-Xaa$_{12}$-Xaa$_{13}$-Ser-Ala-Leu-Arg-His-Tyr-Ile-Asn-Leu-Ile-Thr-Arg-Pro-Arg-Tyr (SEQ ID NO:2), wherein the C-terminus is amidated, Xaa$_7$ and Xaa$_{13}$ are residues of natural amino acids or synthetic residues such that an intramolecular bridge exists between them, Xaa$_8$ and Xaa$_9$ are independently any natural amino acid or synthetic residue, and Xaa$_{10}$-Xaa$_{11}$-Xaa$_{12}$ is either (a) Ala-Arg-Tyr; (b) Arg-Tyr; (c) Tyr; or (d) desXaa$_{10}$-Xaa$_{11}$-Xaa$_{12}$.

A method is provided for diagnosing physiological disorders manifested by an abnormal level of endogenous Y1 receptors, by means of measurement of the amount of a NPY Y1 specific cyclic peptide analog which binds to endogenous Y1 receptor in a biological sample. A method is also provided for detecting physiological disorders including neuroblastoma tumors manifested by an abnormal level of endogenous Y1 receptors by means of administration of a radiolabelled NPY Y1 specific cyclic peptide analog to a host subject followed by radiographic imaging. A method is further provided for therapeutic use of the cyclic peptide NPY analogs in clinical treatment of hypotension and anorexia.

DETAILED DESCRIPTION OF PREFERRED EMBODIMENTS

Terms used herein are intended to have the meaning commonly understood by those skilled in the art unless otherwise indicated. All citations to patents and publications herein are incorporated by reference.

Selective activity characteristic of the centrally truncated NPY cyclic peptide analogs described herein refers to the substantial binding and NPY biological activation of NPY Y1 receptors (Y1 receptor $K_i$ ($IC_{50}$)<50 nM) combined with the lack of substantial binding and biological activation of NPY Y2 receptors (Y2 receptor $K_i$ ($IC_{50}$)>500 nM).

Synthetic residue as used herein refers to D-isomers of naturally occurring amino acids or other entities which may be substituted to provide physicochemical properties to fit the characteristics of the cyclic peptides described herein.

Physiological disorder manifested by an abnormal level of endogenous Y1 receptors as used herein refers to, inter alia, neuroblastoma tumors, and physiological sites and tissues responsible for, or indicative of hypotension, anorexia, and psychiatric disorders manifested by the biological condition of abnormal density of Y1 receptors per tissue weight or radiographically imaged area of biological tissue.

Biological sample as used herein refers to biological tissues and fluids.

Detecting physiological disorders manifested by abnormal levels of the NPY Y1 receptor as used herein refers to localizing the source or indication of physiological disorders such as neuroblastoma tumors, anorexia and hypotension in tissues throughout the body.

Effective amount as used herein refers to an amount of a cyclic peptide described herein which is effective in substantially relieving symptoms of the disorder.

Host subject as used herein refers to mammals including humans.

The term "analog" includes any polypeptide having an amino acid residue sequence substantially identical to a sequence specifically shown herein in which one or more residues have been conservatively substituted with a functionally similar residue and which polypeptide displays the ability to mimic NPY as described herein.

The abbreviations for the amino acids are in accord with the recommendations of the IUPAC-IUB Joint Commission on Biochemical Nomenclature (Eur. J. Biochem. 1984), 138, 9–37). The symbols represent the L-isomer except when indicated otherwise. In addition: APP, avian pancreatic polypeptide; Boc, tert-butyloxycarbonyl; BOP, (benzotriazol-1-yloxy)tris(dimethylamino)phosphonium hexafluorophosphate; DCHA, dicyclohexylamine; DCM, dichloromethane; DMF, dimethylformamide; Dpr, 2,3-diaminopropionic acid; Dbu, diaminobutyric acid; Agl, aminoglycine; EDT, ethanedithiol; DIC, 1,3-diisopropylcarbodiimide; Fmoc, (fluoren-9-ylmethoxy)carbonyl HOBt, 1-hyrdoxybenzotriazole; MBHA, methylbenzhydrylamine; NMP N-methylpyrrolidone; OFm, fluoren-9-ylmethyl ester; PP, pancreatic polypeptide; PYY, peptide YY; TEAP, triethylammoniumphosphate; TFA, trifluroacetic acid.

The NPY biologically active peptide has a characteristic tertiary structure featuring an intramolecularly stabilized helical structure referred to as the polypeptide fold (PP-fold). NPY is composed of two anti-parallel helices, an N-terminal polyproline type II helix (residues 1–8) and a β-turn through positions 9–14 which connects to a long amphipathic α-helix and is held in the folded configuration through hydrophobic interactions between side chains of the α-helix interdigitating with the prolines in the N-terminal section, complete with a C-terminal turn structure from residues 33–36. The PP-fold is stable, even in dilute aqueous solutions, as shown by circular dichroism studies.

Neuroblast tumors, manifested by neuroblastoma cells which have abnormally high levels of the NPY Y1 receptor (80,000–125,000 per cell), cause a very high rate of clinical mortality in children. The high rate of mortality is largely due to the lack of early detection and the corollary stage progression and subsequent metastases. The ability to detect and localize neuroblastoma tumors at an early stage will clearly contribute significantly to the ability to control the disease via surgery, irradiation, and chemotherapy.

NPY is also the most powerful appetite stimulant known. (Wilding, J. P. H. et al., Journal of Endocrinology, 132:299–302 (1992)). The centrally evoked food intake (appetite stimulation) effect is predominantly mediated by NPY Y1 receptors and causes increase in body fat stores and obesity (Stanley, B. G. et al., Physiology and Behavior, 46:173–177 (1989)).

Since NPY plays a significant role in normal physiological and pathological processes, the importance of developing synthetic receptor-specific Y1 agonists is evident. The object of the present invention is to optimize the selective binding affinity of stable cyclic NPY peptides to the NPY Y1 receptor through the introduction of an intramolecular bridge and the manipulation of component amino acids to provide biologically stable analogs which have valuable diagnostic and pharmacological properties. Herein described is the synthesis and binding activities of a family of centrally truncated NPY cyclic peptide analogs. These analogs demonstrate selective in vivo binding and activation of NPY Y1 receptors. The family of centrally truncated NPY cyclic peptide analogs described herein mediate vasoconstriction without affecting catecholamine release or propagating the physiological effects such as decrease in cardiac contractility (inotropy) associated with the activation of NPY Y2 receptors. Compounds described herein are derived from porcine NPY: Tyr-Pro-Ser-Lys-Pro-Asp-Asn-Pro-Gly-Glu-Asp-Ala-Pro-Ala-Glu-Asp- Leu-Ala-Arg-Tyr-Tyr-Ser-Ala-Leu-Arg-His-Tyr-Ile-Asn-Leu-Ile-Thr-Arg-Gln-Arg-Tyr (SEQ ID NO:1), which has demonstrated the $K_i$ ($IC_{50}$) values for NPY Y1 and Y2 receptors of 2.0 nM and 0.3 nM, respectively, using human SK-N-MC and SK-N-BE2 cells, as described infra. The human SK-N-MC cell line expresses the $Y_1$ receptor subtype and binds NPY with a $K_i$ of 2.0±0.1 nM. This binding is to a single class of receptors numbering approximately 120,000 per cell. The human SK-N-BE2 cells bind NPY to the Y2 receptor with a $K_i$ of 0.3±0.1 nM.

Optimization of NPY Y1 receptor binding affinity is developed by the coordinated manipulation of the position of an intramolecular bridge as well as manipulation of the amino acid composition and length of the cyclic peptide analogs. Cyclic peptide NPY analogs described herein preferably have their secondary structure covalently stabilized through the introduction of disulfide or lactam intramolecular bridges. Intramolecular bridges may also be formed by other means known to those skilled in the art, for example, amide bonds, intramolecular ionic interaction, metal chelation, or polyamine templates may be used.

The stable and potent C-terminally amidated family of centrally truncated NPY cyclic peptide analogs described herein which are capable of binding and activating NPY Y1 receptors without substantially binding and activating Y2 receptors have the following formula (SEQ ID NO:2):

Tyr-Pro-Ser-Lys-Pro-Asp-$Xaa_7$-$Xaa_8$-$Xaa_9$-$Xaa_{10}$-$Xaa_{11}$
-$Xaa_{12}$-$Xaa_{13}$-Ser-Ala-Leu-Arg-His-Tyr-Ile-Asn-Leu-Ile-Thr-Arg-Pro-Arg-Tyr wherein the C-terminus is amidated, $Xaa_7$ and $Xaa_{13}$ are independently natural amino acid residues or synthetic residues such that an intramolecular bridge exists between such residues, $Xaa_8$ and $Xaa_9$ are independently natural amino acid residues or synthetic residues, and $Xaa_{10}$-$Xaa_{11}$-$Xaa_{12}$ can be (a) Ala-Arg-Tyr; (b) Arg-Tyr; (c) Tyr; or (d) des$Xaa_{10}$-$Xaa_{11}$-$Xaa_{12}$.

Residues $Xaa_8$ and $Xaa_9$ of SEQ ID NO:2 constitute "spacer" residues which contribute to the spatial integrity of the PP-fold. Such residues may be independently L- or D-isomers of natural amino acids or artificial moieties including a single entity. A rigid spacer is preferred such as $Pro_8$-$Xaa_9$ with $Xaa_9$ being Gly or D-Ala or the like. $Pro_8$-$Xaa_9$ provides an intramolecular β-turn and allows the N- and C-termini of the compound to align, thus mimicking the structural features essential for NPY binding to Y1 receptors. In a preferred embodiment of the NPY cyclic peptide analogs according to SEQ ID NO:2 residues $Xaa_8$ and $Xaa_9$ are Pro and Gly, respectively. It is further contemplated that amino acids or artificial moieties with similar biophysical properties may be substituted without significant compromise of Y1 binding.

Intramolecular bridges are formed within the peptide analogs of SEQ ID NO:2 between residues $Xaa_7$ and $Xaa_{13}$ through disulfide bonds, lactamization or other means well known to those skilled in the art. A $Cys_7$-$Cys_{13}$ disulfide bond that creates a cyclizing intramolecular bridge in the peptide analogs of SEQ ID NO:2 yields analogs with potent selective NPY Y1 receptor binding properties. Therefore in preferred embodiments of the NPY cyclic peptide analogs according to SEQ ID NO:2, both of the residues, $Xaa_7$ and $Xaa_{13}$ are Cys. Intramolecular bridges of similar length, chirality and physical nature also yield compounds having substantially the same biological binding properties. $Asp_7$-$Dpr_{13}$ approximates the size and physical character of a di-cysteine bridge and yields stable NPY analog compounds of SEQ ID NO:2 with potent selective Y1 binding properties. Therefore an intramolecular bridge composed of $Asp_7$-$Dpr_{13}$ (or $Dpr_7$-$Asp_{13}$) comprises yet another preferred embodiment of SEQ ID NO:2. Other embodiments of SEQ ID NO:2 comprise $Asp_7$-$Dbu_{13}$ and $Asp_7$-$Agl_{13}$. Additional embodiments of the NPY cyclic peptide analogs according to SEQ ID NO:2 are contemplated wherein each of these aforementioned residues which are components of the intramolecular bridge may be reversed in position.

Residues $Xaa_{10}$-$Xaa_{11}$-$Xaa_{12}$ of SEQ ID NO:2 are preferably $Ala_{10}$-$Arg_{11}$-$Tyr_{12}$, but in other preferred embodiments $Xaa_{10}$-$Xaa_{11}$-$Xaa_{12}$ may be completely absent from the cyclic peptide. Residues $Xaa_{10}$-$Xaa_{11}$-$Xaa_{12}$ of SEQ ID NO:2 may also consist of (a) Ala-Arg-Tyr; (b) Arg-Tyr; or (c) Tyr.

Preferred embodiments of the present invention according to SEQ ID NO:2 comprise one of the bridging residue pairs Cys, Cys; Asp, Dpr; Asp, Dbu; or Asp, Agl occupying positions $Xaa_7$ and $Xaa_{13}$ of the NPY cyclic peptide analog; and the dipeptide residue $Pro_8$-$Gly_9$.

Particularly preferred embodiments of the present invention include:

Tyr-Pro-Ser-Lys-Pro-Asp-$Xaa_7$-Pro-Gly-Ala-Arg-Tyr-$Xaa_{13}$ -Ser-Ala-Leu-Arg-His-Tyr-Ile-Asn-Leu-Ile-Thr-Arg-Pro-Arg-Tyr (SEQ ID NO:3) wherein the C-terminus is amidated; and, Tyr-Pro-Ser-Lys-Pro-Asp-Cys-$Xaa_8$-$Xaa_9$ -Ala-Arg-Tyr-Cys-Ser-Ala-Leu-Arg-His-Tyr-Ile-Asn-Leu-Ile-Thr-Arg-Pro-Arg-Tyr (SEQ ID NO:4) wherein the C-terminus is amidated.

The most preferred embodiment of the present invention is the NPY cyclic peptide analog having the sequence:
Tyr-Pro-Ser-Lys-Pro-Asp-Cys-Pro-Gly-Ala-Arg-Tyr-Cys-Ser-Ala-Leu-Arg-His-Tyr-Ile-Asn-Leu-Ile-Thr-Arg-Pro-Arg-Tyr (SEQ ID NO:5) wherein the C-terminus is amidated. The NPY cyclic peptide SEQ ID NO:5 has demonstrated $K_i$ ($IC_{50}$) values for NPY Y1 and Y2 receptors of 5.0 nM, and greater than 1000 nM, respectively, using human SK-N-MC and SK-N-BE2 cells, as described infra.

Other preferred embodiments of the present invention include: Tyr-Pro-Ser-Lys-Pro-Asp-Asp-Pro-Gly-Ala-Arg-Tyr-$Xaa_{13}$-Ser-Ala-Leu-Arg-His-Tyr-Ile-Asn-Leu-Ile-Thr-Arg-Pro-Arg-Tyr (SEQ ID NO:10) wherein the C-terminus is amidated, and $Xaa_{13}$ is Dpr, Dbu or Agl. The NPY cyclic peptide SEQ ID NO:10 wherein $Xaa_{13}$=Dpr, has demonstrated $K_i$ ($IC_{50}$) values for NPY Y1 and Y2 receptors of 38 nM, and greater than 1000 nM, respectively, using human SK-N-MC and SK-N-BE2 cells, as described infra.

A preferred subgenus of the present invention according to SEQ ID NO:2 comprises des$Xaa_{10}$-$Xaa_{11}$-$Xaa_{12}$ which yields NPY cyclic peptide analogs having the sequence:
Tyr-Pro-Ser-Lys-Pro-Asp-$Xaa_7$-$Xaa_8$-$Xaa_9$-$Xaa_{13}$ -Ser-Ala-Leu-Arg-His-Tyr-Ile-Asn-Leu-Ile-Thr-Arg-Pro-Arg-Tyr
(SEQ ID NO:6) wherein the C-terminus is amidated. These compounds mimic the NPY 21–36 C-terminal fragment which binds to the Y1 receptor with higher affinity than longer fragments. A preferred embodiment of this subgenus is Tyr-Pro-Ser-Lys-Pro-Asp-$Xaa_7$-Pro-Gly-$Xaa_{13}$ -Ser-Ala-Leu-Arg-His-Tyr-Ile-Asn-Leu-Ile-Thr-Arg-Pro-Arg-Tyr
(SEQ ID NO:7) wherein the C-terminus is amidated. Another preferred embodiment of this subgenus according to SEQ ID NO:6 includes $Cys_7$-$Cys_{13}$. A particularly preferred embodiment is the cyclic NPY peptide having the sequence:
Tyr-Pro-Ser-Lys-Pro-Asp-Cys-Pro-Gly-Cys-Ser-Ala-Leu-Arg-His-Tyr-Ile-Asn-Leu-Ile-Thr-Arg-Pro-Arg-Tyr
(SEQ ID NO:8) wherein the C-terminus is amidated. The cyclic NPY peptide SEQ ID NO:8 has demonstrated $K_i$ ($IC_{50}$) values for NPY Y1 and Y2 receptors of 32 nM, and greater than 1000 nM, respectively, using human SK-N-MC and SK-N-BE 2 cells, as described infra.

Other preferred embodiments of the present invention according to SEQ ID NO:6 include: Tyr-Pro-Ser-Lys-Pro-Asp-Asp-Pro-Gly-$Xaa_{13}$ -Ser-Ala-Leu-Arg-His-Tyr-Ile-Asn-Leu-Ile-Thr-Arg-Pro-Arg-Tyr (SEQ ID NO:11) wherein the C-terminus is amidated, and $Xaa_{13}$ is Dpr, Dbu or Agl.

All cyclic peptides are synthesized using standard solid phase synthesis and intramolecular bridge techniques currently practiced by those skilled in the art as discussed infra.

Preparation of Cyclic Peptides

The NPY cyclic peptide agonists described herein which are selective for the NPY Y1 receptor can be synthesized by any suitable method, such as by exclusive solid-phase techniques, by partial solid-phase techniques, by fragment condensation, by classical solution addition, or by biosynthesis via recombinant DNA technology. For example, the techniques of solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Synthetic NPY analogs of the invention may also be entirely or partially synthesized by recombinant DNA techniques, which may advantageously be used for large-scale production. Synthesis by the use of recombinant DNA techniques, for purposes of this application, should be understood to include the suitable employment of a structural gene coding for all or an appropriate section of the NPY analog to transform a microorganism, using an expression vector including a promoter and operator together with such structural gene, and causing such transformed microorganism to express the peptide or a fragment of such peptide. A plant or non-human animal may also be used to produce the peptide by gene-farming using such a structural gene in the microinjection of embryos as described in U.S. Pat. No. 4,870,009 issued Sep. 26, 1989.

NPY cyclic peptide analogs having disulfide intramolecular bridges described herein and precursors thereto may be produced via recombinant gene expression in heterologous biological systems. DNA sequences which encode, e.g., SEQ ID NO:5, e.g.:
5'TACCCCTCCAAGCCGGACTGC-
CCGGGCGCCAGATACTGCTCGGCGCTGC-
GACACT ACATCAACCTCATCACCAGGCCCA-
GATAT3'
(SEQ ID NO:9) can be functionally inserted in proper reading frame and orientation into an expression vector as is well understood by those skilled in the art. Oligonucleotides, as well as complementary strands preferably with 5' and/or 3' overhang "sticky ends", are synthesized, preferably using automated synthesizers, such as the Applied Biosystem Inc. Model 380A DNA synthesizer (see also, T. Maniatis et al., *Molecular Cloning, A Laboratory Manual*, second edition, Cold Spring Harbor Laboratory Press, New York (1989)). Well developed commercial bacterial expression vectors and host cells are readily available, as well as isolation/purification materials and protocols for production of biosynthetic polypeptides. Production of a hybrid protein followed by enzymatic cleavage may also be used (e.g., Protein Fusion and Purification System (PFP), New England Biolabs).

Nucleic acid sequences which encode the amino acid sequences of the cyclic peptide NPY analogs described herein are of an exponential sum due to the potential substitution of degenerate codons (different codons which encode the same amino acid). The oligonucleotide sequence selected for heterologous expression is therefore preferably tailored to meet the most common characteristic tRNA codon recognition of the particular host expression system used as well known by those skilled in the art.

Suitable conservative substitutions of amino acids are known to those of skill in this art and may be made generally without altering the biological activity of the resulting cyclic peptide analogs, regardless of the chosen method of synthesis. The phrase "conservative substitution" includes the use of a chemically derivatized residue in place of a non-derivatized residue provided that such polypeptide displays the desired binding activity. D-isomers may also be substituted for the naturally occurring amino acids. Substitutions are preferably, although not exclusively, made in accordance with those set forth in TABLE 1 as follows:

TABLE 1

| Original residue | Conservative substitution |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

Manual Peptide Synthesis

When the peptides of the invention are not prepared using recombinant DNA technology, they are preferably prepared using solid phase synthesis, such as that described by Merrifield, *J. Am. Chem. Soc.*, 85, p 2149 (1964), although other equivalent chemical syntheses known in the art can also be used (the most preferred method is set forth in Example II). Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for NPY analogs can, for example, be prepared by attaching alpha-amino- and side-chain-protected Tyr to a BHA resin.

Common to coupling-type chemical syntheses of peptides is the protection of labile side chain groups of the various amino acid moieties with suitable protecting groups which prevent a chemical reaction from occurring at that site until the protecting group is ultimately removed. Also common is the protection of an alpha-amino group on an amino acid or a fragment while the carboxyl function is undergoing reaction, followed by selective removal of the alpha-amino protecting group to allow subsequent reaction to take place at the amino function location. Accordingly, it is common that, as a step in the synthesis, an intermediate compound is produced which includes each of the amino acid residues located in its desired sequence in the peptide chain with various of these residues having side-chain protecting groups.

In selecting side chain protecting groups to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

Tyr protected by BOC and DCB is coupled to the BHA resin using methylene chloride or dimethylformamide (DMF) as solvent with a suitable coupling reagent. The selection of an appropriate coupling reagent is within the skill of the art. Particularly suitable as a coupling reagent is N,N'-dicyclohexyl carbodiimide (DCC). The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, The Peptides, (Academic Press 1965) in Chapter III and by Kapoor, *J. Phar. Sci.*, 59, pp 1–27 (1970).

Following the coupling of BOC-Tyr(DCB) to the resin support, the alpha-amino protecting group is removed, by using trifluoroacetic acid (TFA) in methylene chloride, TFA alone or with HCl in dioxane. Preferably 50% TFA in methylene chloride is used with 0–5% 1,2 ethanedithiol. The deprotection is carried out at a temperature between about 0° C. and room temperature. Other standard cleaving reagents and conditions for removal of specific alpha-amino protecting groups may be used as described in Schroder & Lubke, pp 72–75.

After removal of the alpha-amino protecting group, the remaining alpha-amino- and side-chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. Each protected amino acid or amino acid sequence is introduced into the solid phase reactor in about a two to fourfold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis can be monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a BECKMAN 990 automatic synthesizer, using a program such as that reported in Rivier et al., *Biopolymers*, 1978, 17, pp.1927–1938.

After the desired amino acid sequence has been completed, the intermediate peptide is removed from the resin support by treatment with a reagent, such as liquid hydrogen fluoride, which not only cleaves the peptide from the resin but also cleaves the alpha-amino protecting group and all remaining side chain protecting groups to obtain the peptide.

Orthogonal systems have been developed in which two or more side-chain protection methods are employed (see, Rivier, J., et al., *J. Med. Chem,*, 16:545–549 (1973); Felix, A., et al., *Int. J. Pept. Protein Res.*", 31:231–238 (1988)). Cyclization via the unprotected side-chain groups proceeds both while the peptide remains attached to the polystyrene resin support and after final cleavage from the resin. Lactam formation is performed on the resin. Activating reagents such as DIC/HOBt and/or BOP are most successfully employed in conjunction with polar solvents such as DMF or NMP.

The reactivity of free sulfhydryl groups of cysteine-containing analogues provides a convenient method for cyclization and is easily performed by air oxidation. Under high dilution conditions, all disulfide peptides are obtained in good yield and purity after HPLC purification.

All peptides of the invention were assembled using standard solid-phase peptide synthesis techniques as described in Example II.

Pharmacological Activity

The family of stable and pharmacologically potent centrally truncated NPY cyclic peptides described herein constitute therapeutic compounds for treatment via selective in vivo binding and activation of NPY Y1 receptors. Upon administration of the Y1 specific cyclic peptide NPY agonists, the stimulation of appetite and increase in body fat stores in host subjects is mediated without affecting catecholamine release or propagating the physiological effects such as decrease in cardiac contractility (inotropy) associated with the activation of Y2 receptors. A method for treatment of anorexia comprises administering to a host subject an effective amount of a cyclic NPY peptide of the present invention to stimulate the appetite and increase body fat stores which thereby substantially relieves the symptoms of anorexia. A method for treatment of hypotension comprises administering to a host subject an effective amount of a cyclic NPY peptide of the present invention to mediate vasoconstriction and increase blood pressure which thereby substantially relieves the symptoms of hypotension. Treatment to relieve symptoms of anorexia and hypotension is therefore effected by administering a NPY cyclic peptide or a nontoxic salt thereof to a host subject as described herein.

NPY cyclic peptides or nontoxic addition salts thereof, combined with a pharmaceutically acceptable carrier to form a pharmaceutical composition, may be administered to mammals, including humans, either intravenously, subcutaneously, intramuscularly, percutaneously, e.g. intranasally, intracerebrospinally, orally or by suppository. The peptide should be at least about 90% pure and preferably should have a purity of at least about 98% when administered to humans. This purity means that the intended peptide constitutes the stated weight % of all like peptides and peptide fragments present. Administration may be employed to raise blood pressure to counteract hypotension or to treat eating disorders such as anorexia; the required dosage will vary with the particular condition being treated, with the severity of the condition and with the duration of desired treatment.

The peptides of the invention can be administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like.

The cyclic peptide Y1 receptor selective NPY agonists of the invention may be administered by any convenient means which will result in delivery of the peptide agonist into the bloodstream in substantial amount. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The cyclic peptides of the invention should be administered under the guidance of a physician. Pharmaceutical compositions will usually contain the peptide in conjunction with a conventional, pharmaceutically-acceptable carrier. Usually, the dosage will be from about 1 to about 200 micrograms of the cyclic peptide per kilogram of the body weight of the host. As used herein all temperatures are °C. and all ratios are by volume. Percentages of liquid materials are also by volume.

Additionally, the peptide NPY analogs described herein can be used in the identification, production and purification of Y1 receptors.

Y1 Affinity Purification

Cyclic NPY peptides described herein are used to affinity purify NPY Y1 receptors from either native biological materials, e.g. human heart tissue (see Example I) or neuroblastoma cells, or from cells which have been engineered to produce the NPY Y1 receptor (Rimland, G., et al., Sequence and Expression of a Neuropeptide Y Receptor cDNA, Mol. Pharmacol. 40:869–875 (1991)). Affinity chromatography techniques are well known to those skilled in the art. A cyclic NPY peptide described herein, is fixed to a solid matrix, e.g. CNBr activated SEPHAROSE according to the protocol of the supplier (Pharmacia, Piscataway, N.J.), and a homogenized/buffered cellular solution containing the molecule of interest, i.e., the NPY Y1 receptor, is passed through the column. After washing, the column retains only the NPY Y1 receptor which is subsequently eluted, e.g., using 0.5M acetic acid or a NaCl gradient.

Diagnostic Immunoassays

Cyclic NPY peptides described herein may be used to identify tissues afflicted with pathological conditions wherein the NPY Y1 receptor is overexpressed or underexpressed thus manifesting tumors (e.g. neuroblastoma), hypotension, anorexia, or other NPY Y1 receptor associated disorders. Assay techniques include both heterogenous and homogenous immunoassay techniques. Heterogenous sandwich assays for the NPY Y1 receptor typically use a specific monoclonal or polyclonal antibody bound to a solid support. Sandwich immunoassays for detecting biological tissue content of Y1 receptor (analyte) are based on reactions wherein antibodies raised against a cyclic peptide NPY analog described herein, e.g., SEQ ID NO:5 and/or the Y1 receptor are used in techniques which are well known to those skilled in the art, e.g., as described in U.S. Pat. No. 5,210,017 which is herein incorporated by reference. An antibody prepared against a cyclic peptide NPY analog described herein, using production methods well known to those skilled in the art, may be affixed to a solid matrix and saturated with the cyclic peptide NPY analog (alternatively a cyclic peptide NPY analog described herein may be affixed directly to a solid matrix as discussed in regard to NPY Y1 purification using an affinity column). The cyclic NPY peptide fixed to the solid matrix is then contacted with tissue sample homogenate which binds NPY Y1 receptors endogenous to the sample. After thorough washing of the solid matrix to remove unbound Y1 receptor, bound Y1 receptor is determined by reacting a radiolabelled anti-Y1 antibody with the formed Y1/cyclic NPY peptide analog/matrix-complex, washing the matrix free of unbound anti-Y1 radio-labelled antibody, and upon elution of the labelled anti-Y1 antibody, counting the label and comparing the results to values from normal tissue.

The solid surface reagent in the sandwich assay is prepared by known techniques for attaching protein material to solid support material, such as polymeric beads, dip sticks, or filter material. These attachment methods generally include non-specific adsorption of the protein typically through a free amine group, to a chemically reactive group on the solid support, such as an activate carboxyl, hydroxyl, or aldehyde group Assays employed herein can be used in an "ELISA" format to detect the quantity of NPY Y1 receptor in a biological sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090, No. 3,850,752; and No. 4,016,043, which are all incorporated herein by reference.

Thus, in preferred embodiments, a cyclic NPY peptide described herein, e.g., SEQ ID NO:5, a polyclonal anti-cyclic NPY peptide antibody, or a monoclonal anti-cyclic NPY peptide antibody is affixed to a solid matrix to form a solid support. A reagent is typically affixed to a solid matrix by adsorption from an aqueous medium although other modes of affixation applicable to proteins and polypeptides well known to those skilled in the art can be used. Useful solid matrices are also well known in the art. Such materials are water insoluble and include the cross-linked dextran available from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

Various heterogenous and homogenous protocols, either competitive or noncompetitive, solution-phase or solid-phase, can be employed in performing an assay method of this invention.

Those skilled in the art will understand that there are numerous well known clinical diagnostic chemistry procedures in which an immunochemical reagent of this invention can be used to form an immunoreaction product whose amount relates to the amount of Y1 receptor present in a body sample. Thus, while exemplary assay methods are described herein, the invention is not so limited.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide fragment, or antibody molecule that is part of an antibody or monoclonal antibody composition of the present invention, or used separately. These labeling atoms or molecules can be used alone or in conjunction with additional reagents. Such labels are themselves well-known in clinical diagnostic chemistry and constitute a part of this invention only insofar as they are utilized with otherwise novel proteins, methods, and/or systems.

The labeling means can be a fluorescent labeling agent that chemically binds to antibodies without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In certain preferred embodiments, the indicating group is an enzyme, such as horseradish peroxidase (HRP), glucose oxidase or the like. In such cases where the principal indicating group is an enzyme, such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{126}$I, $^{131}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such as $^{111}$indium or $^3$H.

The labeling of antibodies, polypeptides, and proteins, is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

Radioiodination of cyclic peptides, anti-cyclic peptide antibodies and immunochemically purified goat anti-mouse Ig is performed utilizing the known IODOGEN iodination procedure, and Iodogen obtained from Pierce Biochemicals. IODOGEN iodination is utilized to prepare the antigens and antibodies for use in solid phase radioimmunoassays as discussed. Radio-labeling can also be performed employing chloramine T or Lacto peroxidase, and the like.

Homogenous assays, which are carried out in a solution without the presence of a solid phase, can also be used. A number of suitable assays are disclosed in U.S. Pat. Nos. 3,817,837, and 3,996,345 which are herein incorporated by reference. In a homogeneous assay diagnostic configuration, an antibody binding to an analyte produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaption of these methods to the cyclic peptides of the present invention follows conventional methods for preparing homogeneous assay reagents.

Direct Binding Assay

The cyclic NPY peptides described herein are also used for diagnosing pathological disorders manifested by abnormal levels of endogenous NPY Y1 receptors by measuring the binding of such analogs to tissues and comparing the determined binding level to that of normal tissues under identical conditions. Radiolabels such as $^{35}$S, $^{32}$P, $^{127}$I or $^{125}$I or other biochemical means of identification such as spin label, or enzymatic complexes as described supra may be used to label the cyclic peptides as commonly practiced by those skilled in the art. Biological samples such as blood or tissue or homogenized tissue (0.1 g or less is sufficient) is subjected under physiological conditions, preferably by gentle mixing in autoclaved phosphate buffered saline solution, to between 100 ng and 1 mg of a labelled cyclic NPY peptide, e.g., SEQ ID NO:5, as described herein. Subsequent to kinetic equilibrium the biological sample is cleared of unbound label preferably by washing the sample in sterile phosphate buffered saline, 3× by gentle centrifugation and resuspension of the sample, using techniques well known to those skilled in the art. After the final wash the sample is preferably recentrifuged and the pelleted label is quantitatively measured in a scintillation counter. The quantity of labelled cyclic NPY peptide bound to the biological sample is compared to the quantity of labelled cyclic peptide which binds to normal biological samples under identical conditions. Normal tissue levels of NPY Y1 receptor are not of significant concentration, accordingly levels manifested in neuroblastoma and the like are easily distinguishable from background levels of NPY Y1.

Radioimaging

The invention is also directed to a method for detecting physiological disorders such as neuroblastoma tumors manifested by abnormal levels of the NPY Y1 receptor, comprising: administering to a host subject at least one radiolabelled cyclic NPY peptide according to the invention; and subsequently detecting the presence and location of the label with imaging technology well known to those of ordinary skill in the art of nuclear medicine. Freeman et al., *Freeman and Johnson's Clinical Radionuclide Imaging* 3, (1) (1984) Grune & Stratton, New York; Ennis et al., *Vascular Radionuclide Imaging: A Clinical Atlas,* John Wiley & Sons, New York (1983). A preferred method is provided for localization of a neuroblastoma tumor which is a physiological disorder manifested by an abnormal level of NPY Y1 receptor(s), e.g., 80,000–125,000/cell.

A wide range of radioactive species may be employed for providing the radioactive label for use in the invention. Suitable radioactive labels include, but are not limited to $^{99m}Tc$, $^{123}I$, $^{111}In$, $^{68}Ga$, $^{18}F$, $^{125}I$, $^{131}I$, $^{113m}In$, $^{76}Br$ and $^{67}Ga$. $^{99m}Tc$, $^{123}I$, $^{111}In$, $^{68}Ga$, and $^{18}F$ are preferred. Radioactive atoms can be attached to cyclic peptides by methods well known to those skilled in the art. See, *Science* 220:613–615; *Int. J. Nucl. Med. Biol.* 12:3–8; *J. Nucl. Med.* 27:685–693 and *J. Nucl. Med.* 26:293–299. Arano et al., *Bioconjugate Chemistry* 2:71–76 (1991); Eisenhut et al., *J. Labelled Comp. Radiopharm* 30:198–199 (1991) (abs.); Garg et al., *Bioconjugate Chemistry* 2:44–49 (1991); Knight et al., *Thromb. Haemostas* 46:593–596 (1981); Mather et al., *J. Nucl. Med.* 31:692–697 (1990).

The cyclic NPY peptides disclosed herein may also be modified for attachment of metallic radiolabels by addition of bifunctional chelating groups. Krejcarek et al., *Biochem Biophys Res. Commun.* 77:581–585 (1977); Fritzberg et al., *Proc. Natl. Acad. Sci. USA* 85:4025–4029 (1988); Sundberg et al., *Nature* 250:587–588 (1974); Bhargava et al., *J. Labelled Comp. Radiopharm.* 30:216–218 (1991) (abs.); Benisek et al., *J. Biol. Chem.* 243:4267–4271 (1968).

The radiolabelled cyclic peptides may be combined with any pharmaceutically acceptable carrier suitable for parenteral, preferably intravenous administration. Thus, the radiolabelled cyclic peptides may be formulated according to conventional methods for preparing peptide agents for parenteral administration. The intravenous carrier most advantageously comprises a pharmaceutically acceptable buffer solution such as phosphate buffered saline, preferably in combination with a pharmaceutically acceptable compound for adjusting isotonic pressure, such as mannitol or sorbitol.

Compositions for parenteral administration, including intravenous injection, may be in the form of lyophilizates or solutions. The resulting formulations will contain an amount of the radiolabelled cyclic NPY peptides effective for imaging.

The concentration of radiolabelled polypeptides in the composition is not critical to practice the method of invention. When administered as a bolus injection to an average 70 kg human, the concentrations of labelled polypeptides preferably range from about 0.025 to about 3 mg/ml (weight of labelled cyclic peptide per volume of composition). When administered as a slow infusion into the bloodstream, effective concentrations of the labelled polypeptides include but are not limited to about 0.01 to about 0.5 µg/ml.

Practical dosages of cyclic NPY peptides labelled with preferred radionuclides for single administration to a 70 kg standard sized human are expressed in terms of the mass of labelled cyclic peptide and amount of radioactivity. Practical dosages of cyclic NPY peptides radiolabelled with preferred radionuclides are as follows:

| Radionuclide | Range of Radioactivity | Mass of Labelled Peptide |
|---|---|---|
| $^{99m}Tc$ | 2–50 mCi | 5 µg–2 mg |
|  | (10–30 mCi preferred) | (30 µg–500 µg preferred) |
| $^{123}I$ | 1–30 mCi | 0.5 µg–1 mg |
|  | (5–20 mCi preferred) | (3 µg–50 µg preferred) |
| $^{111}In$ | 0.1–7 mCi | 0.5 µg–1 mg |
|  | (1–3 mCi preferred) | (5 µg–100 µg preferred) |
| $^{68}Ga$ | 0.1–7 mCi | 0.5 µg–1 mg |
|  | (1–3 mCi preferred) | (5 µg–100 µg preferred) |
| $^{18}F$ | 1–20 mCi | 0.5 µg–1 mg |
|  | (5–15 mCi preferred) | (50 µg–500 µg preferred) |

The rate of administration of radiolabelled cyclic peptides described herein and the total dosage depends on a variety of factors such as the particular cyclic peptide employed to carry the radiolabel, and the site of the body which is subject to imaging. The dosage may range, for example, from about 0.25 µg to about 2 mg of radiolabelled polypeptide per patient dose. Most preferably, the dosages range from about 2 µg to about 1 mg per patient dose.

The effect of radiolabelling the cyclic peptides depends upon the particular radionuclide used. The radiation dosimetry, which depends upon the biodistribution kinetics of the particular radionuclide used, is easily determined by those skilled in the art of nuclear medicine. Methods for determining the appropriate degree of radiolabelling are known to those skilled in the art. According to a method of ex vivo imaging, at least one radiolabelled cyclic peptide is injected or infused into a peripheral vein such as the antecubital of the host subject. A gamma camera is used to externally follow the distribution of the imaging agent in the host subject's body. An image indicative of the presence of Y1 receptor "hot spots" (foci of radiotracer accumulation) or absence of normal background is obtained. Alternatively, tomographic images may be acquired using a SPECT (Single Photon Emission Computed Tomography) or PET (Positron Emission Tomography) camera. The images are acquired at one or more intervals between 1 and 6 hours post injection. Details regarding methods of imaging radionuclides in vivo and vascular imaging in particular are available in standard textbooks. Freeman et al., Freeman and Johnson's Clinical Radionuclide Imaging, 3rd. ed. Vol. 1 (1984) Grune & Stratton, New York; Ennis et al. Vascular Radionuclide Imaging: A Clinical Atlas, John Wiley & Sons, New York (1983).

While the invention has been described with reference to particular embodiments, methods, construction, and use, it will be apparent to those skilled in the art that various changes and modifications can be made without departing from the invention.

EXAMPLE I

Y1 Affinity Purification

To selectively isolate NPY Y1 receptors which bind to cyclic peptide defined by SEQ ID NO:5, 350 g heart tissue is homogenized in 700 ml of standard binding buffer containing 50 mM sodium phosphate, 100 mM sodium chloride, 25 mM EDTA, 0.1 volume percent sodium azide (SPEA) containing 10 mM magnesium chloride, 2 mM phenylmethyl-sulfonylfluoride (PMSF), 2.8 µg/ml leupeptin and 7 µg/ml aprotinin. The homogenate is divided into 500 ml centrifuge buckets and spun at 3000 rpm for 10 minutes in a centrifuge to separate nuclei and particulate matter. The supernatant is decanted, and the pellet is solubilized by the addition of an aqueous solution of NP-40 liquid detergent at a concentration of about 0.2% by volume and by stirring at 4° C. for 1 hour. NP-40 (Nonidet P-40) is a detergent consisting of an octylphenol-ethylene oxide condensate containing an average of nine moles of ethylene oxide per mole of phenol and is available from a number of suppliers, including Fluka Chemical Corporation and Sigma Chemical Company. The NP-40 employed was a >99% pure substance obtained from Fluka Chemika-BioChemika, Ronkonkoma, N.Y., 11779. The mixture is then re-centrifuged at 5000 × g for 15 minutes at 4° C., and the supernatant decanted. The resultant pellet is re-extracted by the addition of 400 ml of binding buffer, and the mixture was recentrifuged as described above without the addition of NP-40. The re-extraction procedure was repeated four times. All the resulting supernatants are pooled and then diluted to a final volume of 4 L with binding buffer.

1 ml of granular AFFIGEL chromatographic media (Bio-Rad) is washed with 50 ml of distilled water at 4° C. 1 mg of cyclic peptide SEQ ID NO:5 is then dissolved in 7 ml of coupling buffer which was 100 mM Hepes, pH 7.4. The AFFIGEL media is added to the mixture, and the container is rotated overnight at 4° C., allowing the cyclic peptide to couple to the media in a total volume of 10 ml. The solid phase is then left to settle under gravity, and the supernatant is decanted. Unreacted groups on the AFFIGEL media are then blocked by exposing the solid phase to 1M ethanolamine/HCL pH 8.0 and rotating in a suitable container for 1 hour at 25° C. The resulting cyclic peptide-solid phase conjugate is transferred to a sintered glass funnel and washed sequentially with ten 50 ml batches each containing 50 mM sodium acetate-formate/20% acetonitrile buffer, pH 3.0 and 100 mM Hepes pH 7.4. The cyclic peptide-solid phase conjugate is then finally diluted by thoroughly mixing with 9 mls of cold, unactivated granular SEPHAROSE 4B, and this dilute mixture is used as the media for the 1st step of the affinity chromatographic separation.

Media for a 2nd step separation is prepared as described above except that no dilution with cold unactivated Sepharose 4B is used, so that the 1 ml of granular AFFIGEL-CRF conjugate alone is employed to treat the much smaller volume of material.

The 4 liters of extract are then exposed to the 10 ml of diluted CRF-solid phase conjugate by stirring this chromatographic media with the extract overnight at 4° C. After exposure, the solid phase is recovered by filtering the 4 L extract through a coarse 600 ml sintered glass funnel. The solid phase is then washed off the sintered glass with 0.9% NaCl and transferred to a BIORAD ECONO column (20× 2.5 cm) where it is further washed with approximately 200 mls of 0.9% NaCl. The bound Y1 receptors are then desorbed with 50 mL of elution buffer, i.e. 80% 50 mM sodium acetate-formate buffer/20% acetonitrile, pH 3.0, containing 0.1% by volume bovine serum albumin (BSA); ten 5 ml fractions were sequentially collected throughout this elution.

Active fractions are then pooled, and the pH is adjusted to about 7.5 with 1M tris base, providing approximately 15 ml of eluant. This eluant was then percolated at 4° C. 5 times over the undiluted cyclic peptide-solid phase conjugate which had been loaded into a BIORAD ECONO column (0.7×10 cm). The solid phase conjugate column is then washed sequentially with 40 mls of 0.9% NaCl and 15 mls of 80% 50 mM sodium acetate-formate/ 20% acetonitrile buffer, pH 6.8. Bound Y1 receptors are then finally eluted in five 0.5 ml fractions using the same elution buffer which is used in eluting the proteins from the first affinity chromatography step but without including any BSA.

The active fractions which elute from this solid phase column are pooled and then concentrated to approximately 100 µl under vacuum in a SPEED-VAC™ concentrator.

EXAMPLE II

Cyclic Peptide Synthesis

All peptides are synthesized manually using the Boc-strategy on MBHA resin prepared by methods previously described in Boublik, J., et al., *J. Med. Chem.*, 32:597–601 (1989). Side-chain protection of α-Boc amino acids (Bachem, Torrance, Calif.) is as follows: Arg(Tos), Asp (β-OcHx or β-OFm), Cys (S-p-Mob), Dpr-(Fmoc), Glu (γ-OcHx or γ-OFm), His(Tos)•DCHA, Lys (2ClZ or Fmoc), Ser(Bzl), Thr(Bzl), and Tyr(2BrZ). Asn and Gln are coupled in the presence of a 2-fold excess of 1-hydroxybenzotriazole. His(Tos)•DCHA is coupled with a 2-fold excess of BOP in the presence of diisopropylethylamine. Removal of the Boc group is accomplished by treatment of the peptide-resin with 60% TFA in DCM in the presence of 1% EDT. The protected peptide-resins are cleaved in anhydrous HF in the presence of 3% anisole at 0° C. for 1.5 h. Crude peptides are precipitated and washed with diethylether, then extracted from the resin and other organic material with water, and lyophilized.

Compounds containing lactam bridges are assembled using Fmoc side-chain protection of the β-amino group of DDpr and the flyorenyl methyl ester protection of the γ-carboxyl of Glu, which is removed by; two treatments of 20% piperidine in DMF for 10 and 15 min. Lactam formation then proceeds on the resin by the method of Felix, A., et al., *Int. J. Pept. Protein Res.*, 31:231–238 (1988), in the presence of 3 equiv of BOP and diisopropylethylamine or BOP/HOBt/diisopropylethylamine in DMF for 12–48 h. Completeness of coupling is monitored every 8 h with ninhydrin after thorough washings using DCM, MeOH, and DCM. If incomplete, fresh coupling reagents are added. For more difficult bridge formations, DIC/HOBt in DCM or DMF are utilized as a secondary coupling reagent.

Cyclization of free sulfhydril-containing analogs is performed following HF cleavage by stirring a dilute solution of the peptide (250 mg/L) in 0.07M NH$_4$OAc (pH 6.8) at 4° C. for 24 h. Completion of cyclization is monitored by the Ellman test and HPLC. Upon complete oxidation, peptide solution is concentrated on a BO-REX- 70 column (100 mL) and eluted with 40% HOAc. A powder is obtained after lyophilization of the diluted peptide-containing fractions.

Crude peptides are purified by preparative reverse-phase HPLC as described in Rivier, J., et al., "Reversed-Phase High-Performance Liquid Chromatography: Preparative Purification of Synthetic Peptides", *J. Chromatogr.*, 288:303–328 (1984), and Hoeger, et al., "Preparative Reversed Phase High Performance Liquid Chromatography: Effects of Buffers pH on the Purification of Synthetic Peptides", *Biochromatography*, 2(3):134–143 (1987), on a WATERS DELTA Prep LC 3000 system equipped with a WATERS 1000 Prep Pak Module and a SHIMADZU SPD-6A variable wavelength UV detector. The cartridges used are hand packed in-house in WATERS polyethylene sleeves and frits and VYDAC C$_{18}$ packing material (15–20 µm particle size, 30 nm pore size). The material is eluted (95–20 µm particle size, 30 nm pore size). The material is eluted (95 mL/min) using a linear TEAP (buffer A)/60% MeCN in TEAP (pH 2.25 or 5.2) (buffer B) gradient; acceptable fractions are pooled, reloaded onto the preparative cartridge, and desalted in 0.1% TFA/MeCN. Final products are 95% pure by HPLC analysis.

EXAMPLE III

Cyclic Peptide Characterization

Purified cyclic peptides are subjected to HPLC analysis (VYDAC $C_{18}$ column, on a PERKIN-ELMER Series 400 Liquid Chromatograph, KRATOS Spectroflow 757 UV detector, and HEWLETT-PACKARD® Model 3390A integrator), amino acid analysis (hydrolysis in 4N methanesulfonic acid at 110° C. for 24 h, followed by ion-exchange chromatography and postcolumn derivatization with o-phthalaldehyde), and LSIMS analysis measured with a JEOL JMS-HX110 double focusing mass spectrometer (JOEL, Tokyo, Japan) fitted with a $Cs^+$ gun. Samples are added directly to a glycerol and 3-nitrobenzyl alcohol (1:1) matrix. Daughter ion spectra of carbiomide amidine analogues are measured using a linked field scan at constant B/E ratio.

Circular dichroism (CD) measurements are obtained with an AVIV® Model 62DC spectropolarimeter (Aviv Associates, Lakewood, N.J.) under control of the manufacturer's operating system (60DS) using 0.5-mm cuvettes thermostated at 20° C. and signal averaging four scans in the range 190–250 nm. Data is collected at 1.0 -nm intervals with a 2.0-s integration time and a spectral bandwidth of 2.0 nm. Spectra of compounds is collected under two sets of buffer conditions: (1) in 0.01M sodium phosphate, 0.05M sodium chloride (pH 7.40), and (2) the above buffer diluted 70/30 (v/v) with 2,2,2 -triflyoroethanol. Concentrations are based on the calculated molecular weight of the TFA salt of the purified lyophilized peptide assuming a water content of 7% and are used for the calculation of residue molar elipticites; water content is not routinely determined. Residue molar elipticites are calculated based on the number of residues in each analogue, irrespective of the presence of side chain-side chain amide bonds.

EXAMPLE IV

Receptor binding assays are performed using the human neuroblastoma SK-N-MC cells $Y_1$ receptors) and the SK-N-BE(2) cells ($Y_2$ receptors). Cells are grown to confluence in 100-mL plates, trypsinized, and plated into 24 microwells plates (105 cells per well). Media for SK-N-MC cells is MEM Eagles (500 mL) buffer, containing L-glutamine (10 Ml, 200 mM, penicillin/streptomycin (5 Ml.10 000 mg/mL), nonessential amino acids (5 mL, 11 mg/mL), fetal calf serum (50 mL, 10%), and 500 µL of fungiyorl. Media for SK-N-BE(2) cells is DME-F12 (500 mL) buffer, containing L-glutamine (10 mL, 200 mM), penicillin/streptomycin (5 mL, 10 000 mg/mL), fetal calf serum (50 mL, 10%), and 500 µL of fungiyorl. After 1 day for the SK-N-BE(2) and 2 days for the SK-N-MC, the cells are grown to the appropriate density and are used for binding assays $Y_1$ and $Y_2$ NPY receptor subtypes can be differentiated by their abilities to bind C-terminal fragments such as $NPY_{13-36}$ (Feinstein, R., et al., *J. Med. Chem.*, 35:2836–2843 (1992)). $NPY_{13-36}$ displaces [$^{125}$I] PYY from SK-N-MC cells with a $K_i$ of 460±62 nM. This low affinity shows that the NPY receptors on the SK-N-MC cell line are of the $Y_1$ subtype. $NPY_{13-36}$ displaces [$^{125}$I]PYY with a $K_i$ of 0.80±0.20 nM. This high affinity demonstrates that the NPY receptors on the SK-N-BE2 cell line are of the $Y_2$ subtype.

The human SK-N-MC cell line expresses the $Y_1$ receptor subtype and binds NPY with a $K_i$ of 2.0±0.1 nM. This binding is to a single class of receptors (P=0.030) numbering approximately 120,000 per cell. The human SK-N-BE 2 cell line is similarly valuable for testing analogs. The cells bind NPY to two classes of receptors (P<0.0001) with $K_i$'s of 0.3±0.1 and 180±110 nM. The high affinity receptors, which are of the $Y_2$ subtype, number approximately 25,000 per cell.

Saturation binding experiments are performed for both the SK-N-MC and SK-N-BE2 cell lines using [$^{125}$I]PYY as the radioligand. The Scatchard plot of the [$^{125}$I]PYY saturation binding data obtained for the SK-N-BE2 cells is nearly linear. The slope of the line filing the data was $-3.16 \times 10^{10}$, corresponding to an affinity constant $K_D$ of 0.080 nM obtained for PYY in competitive binding experiments. The slope of the corresponding Hill plot for the data is equal to 1.03, indicating that no cooperativity exists between the high and low affinity binding sites observed for the SK-N-BE2 cells.

Binding Experiments

Peptides to be tested are prealiquoted at 100 µg/Ml in 100 µL of solution in MILLI-Q™ water (Millipore, U.S.A.). Solutions of peptides in different concentrations (seven doses from $10^{-6}$ to $10^{-10}$M) are prepared in binding buffer (0.30M sucrose, 10 mM HEPES, 0.1% BSA, and pH is adjusted to 7.4 with NaOH). Microwell plates are precoated with p(Lys$_2$-Ala) (100 µL of 0.2 g/L) in doubly distilled $H_2O$ at 37° C. for 1 min followed by replacement with 400 µL of binding buffer per well and stored at 37° until all plates are pretreated. Trace ([$^{125}$I]PYY from NEN, 2200 Ci/mmol) is diluted to 15,000 cpm/50 µL. Each peptide solution (50 µL) is tested in triplicate in the presence of 50 µL of trace. Nonspecific binding is determined in the presence of $10^{-6}$ M cold peptide. After 45 min of incubation at 37° C., the cells are washed with 250 µL of ice-cold binding buffer and lysed with lysis buffer (8M urea, 3M acetic acid, 2% trition). For each well, buffer is transferred to a tube for counting. The content of each well is counted using a Micromedic$_\gamma$ counter. Binding data is analyzed using the nonlinear regression analysis program LIGAND™ (Biosoft, McPhearson modification (1985) of original method of Munmson & Fobard) which iteratively optimizes variables (included standard error) describing a sigmoid curve.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. It should also be understood that all of the amino acid sequences provided herein as examples of cyclic NPY peptides have an intramolecular bridge between the residues at positions 7 and 13 or their counterparts, e.g., at positions 7 and 10; 7 and 11; or 7 and 12, in shortened analogs.

Various features of the invention are emphasized in the claims which follow.

What is claimed is:

1. A cyclic peptide having selective bioactivity for NPY Y1 receptors of the formula (SEQ ID NO:3):

Tyr-Pro-Ser-Lys-Pro-Asp-Xaa$_7$-Pro-Gly-Ala-Arg-
Tyr-Xaa$_{13}$-Ser-Ala-Leu-Arg-His-Tyr-Ile-Asn-Leu-Ile-Thr-Arg-Pro-Arg-Tyr, wherein the C-terminus is amidated and wherein residues Xaa$_7$ and Xaa$_{13}$ are selected from the group consisting of the pairs: Cys, Cys; Asp, Dpr; Asp, Dbu; and Asp, Agl, respectively.

2. A cyclic peptide according to claim 1 having the formula (SEQ ID NO:5):

Tyr—Pro—Ser—Lys—Pro—Asp—Cys—Pro—Gly—Ala—Arg—
|⎯⎯⎯⎯⎯⎯⎯⎯⎯⎯⎯⎯⎯⎯⎯⎯⎯⎯⎯⎯|
Tyr—Cys—Ser—Ala—Leu—Arg—His—Tyr—Ile—Asn—Leu—Ile—Thr—Arg—Pro—Arg—Tyr, wherein the C-terminus is amidated.

3. A cyclic peptide having selective bioactivity for NPY Y1 receptors of the formula (SEQ ID NO:7):

```
                            |⎯⎯⎯⎯⎯⎯⎯⎯⎯⎯⎯|
        Tyr—Pro—Ser—Lys—Pro—Asp—Xaa₇—Pro—Gly—Xaa₁₃—Ser—
Ala—Leu—Arg—His—Tyr—Ile—Asn—Leu—Ile—Thr—Arg—Pro—Arg—Tyr,
``` wherein the C-terminus is amidated and wherein residues $Xaa_7$ and $Xaa_{13}$ are selected from the group consisting of the pairs: Cys, Cys; Asp, Dpr; Asp, Dbu; and Asp, Agl, respectively.

4. A cyclic peptide according to claim 3 having the formula (SEQ ID NO:8):

Tyr-Pro-Ser-Lys-Pro-Asp-Cys-Pro-Gly-Cys-Ser-Ala-Leu-Arg-His-Tyr-Ile-Asn-Leu-Ile-Thr-Arg-Pro-Arg-Tyr, wherein the C-terminus is amidated.

5. A cyclic peptide according to claim 1 wherein $Xaa_7$ is Asp and $Xaa_{13}$ is Dpr.

* * * * *

UNITED STATES PATENT AND TRADEMARK OFFICE
CERTIFICATE OF CORRECTION

PATENT NO. : 5,569,742
DATED : October 29, 1996
INVENTOR(S) : Kirby, et al.

It is certified that error appears in the above-indentified patent and that said Letters Patent is hereby corrected as shown below:

Column 18, line 45, correct the spelling of "sulfhydril-containing" to --sulfhydryl-containing--.

IN THE CLAIMS Column 25, lines 56-59, Claim 1, change "Tyr-Pro-Ser-Lys-Pro-Asp-Xaa$_7$-Pro-Gly-Ala-Arg-Tyr-Xaa$_{13}$-Ser-Ala-Leu-Arg-His-Tyr-Ile-Asn-Leu-Ile-Thr-Arg-Pro-Arg-Tyr," to --Tyr-Pro-Ser-Lys-Pro-Asp-Xaa$_7$-Pro-Gly-Ala-Arg-Tyr-Xaa$_{13}$-Ser-Ala-Leu-Arg-His-Tyr-Ile-Asn-Leu-Ile-Thr-Arg-Pro-Arg-Tyr--.

Signed and Sealed this

Third Day of June, 1997

Attest:

BRUCE LEHMAN

*Attesting Officer*  *Commissioner of Patents and Trademarks*